(12) United States Patent
Park et al.

(10) Patent No.: US 9,132,091 B2
(45) Date of Patent: Sep. 15, 2015

(54) OIL-IN-WATER TYPE NANO-EMULSION COMPOSITION AND METHOD FOR PREPARING SAME

(75) Inventors: Sung Il Park, Seoul (KR); Youn Joon Kim, Seoul (KR); Sang Hoon Han, Suwon-si (KR)

(73) Assignee: Amorepacific Corporation, Seoul (KR)

( * ) Notice: Subject to any disclaimer, the term of this patent is extended or adjusted under 35 U.S.C. 154(b) by 32 days.

(21) Appl. No.: 13/635,784

(22) PCT Filed: Mar. 22, 2011

(86) PCT No.: PCT/KR2011/001953
§ 371 (c)(1),
(2), (4) Date: Sep. 18, 2012

(87) PCT Pub. No.: WO2011/118958
PCT Pub. Date: Sep. 29, 2011

(65) Prior Publication Data
US 2013/0011454 A1    Jan. 10, 2013

(30) Foreign Application Priority Data
Mar. 23, 2010  (KR) .................. 10-2010-0025834

(51) Int. Cl.
| | | |
|---|---|---|
| *A61K 8/02* | (2006.01) | |
| *A61K 9/107* | (2006.01) | |
| *A61K 8/06* | (2006.01) | |
| *A61Q 19/00* | (2006.01) | |
| *A61K 8/34* | (2006.01) | |
| *A61K 8/37* | (2006.01) | |
| *A61K 8/55* | (2006.01) | |
| *A61K 8/60* | (2006.01) | |
| *A61K 8/63* | (2006.01) | |
| *A61K 8/86* | (2006.01) | |

(52) U.S. Cl.
CPC ............... *A61K 9/1075* (2013.01); *A61K 8/062* (2013.01); *A61K 8/345* (2013.01); *A61K 8/37* (2013.01); *A61K 8/375* (2013.01); *A61K 8/553* (2013.01); *A61K 8/60* (2013.01); *A61K 8/63* (2013.01); *A61K 8/86* (2013.01); *A61Q 19/00* (2013.01); *A61K 2800/21* (2013.01)

(58) Field of Classification Search
CPC ....................................... A61Q 19/00
See application file for complete search history.

(56) References Cited

U.S. PATENT DOCUMENTS

| | | | | |
|---|---|---|---|---|
| 4,478,853 | A * | 10/1984 | Chaussee | ....................... 514/772 |
| 4,533,254 | A | 8/1985 | Cook et al. | |
| 2005/0287104 | A1 * | 12/2005 | Aubrun-Sonneville et al. | ..................... 424/70.22 |
| 2007/0213234 | A1 | 9/2007 | Yaghmur et al. | |

FOREIGN PATENT DOCUMENTS

| | | | |
|---|---|---|---|
| EP | 0832643 | A2 * | 4/1998 |
| JP | 2001055308 | | 2/2001 |
| KR | 100540166 | B1 | 12/2005 |
| KR | 100623013 | B1 | 9/2006 |
| KR | 100654841 | B1 | 11/2006 |
| KR | 100740598 | B1 | 7/2007 |
| KR | 1020070083367 | A | 8/2007 |
| KR | 100874877 | B1 | 12/2008 |

OTHER PUBLICATIONS

I.R. Flockhart et al. "Nanoemulsions derived from lanolin show promising drug delivery properties." 1998 J. Pharm. Pharmacol.
PCT International Search Report for PCT/KR2011001953 dated Nov. 2, 2011. 7 pages.

* cited by examiner

*Primary Examiner* — Ali Soroush
(74) *Attorney, Agent, or Firm* — Jansson Munger McKinley and Shape Ltd.

(57) ABSTRACT

The present invention relates to an oil-in-water (O/W) type nano-emulsion composition comprising an oil component containing oil and a polyethylene glycol ester-based emulsifier; and a water component containing a polyol or a polyol derivative. The present invention also relates to a cosmetic composition comprising the oil-in-water type nano-emulsion composition, and to a method for preparing the oil-in-water type nano-emulsion composition. According to the present invention, a nano-sized low-viscosity emulsion having a high inner phase can be obtained through the method that is different from the conventional methods of phase inversion temperature emulsification or high pressure emulsification, thereby significantly improving the stability of the emulsion. In addition, the nano-emulsion composition of the present invention can be added to a variety of cosmetic compositions having a variety of methods of use and can thus deliver active ingredients to the skin effectively since it has small-sized particles.

6 Claims, No Drawings

ND IN-WATER TYPE NANO-EMULSION COMPOSITION AND METHOD FOR PREPARING SAME

TECHNICAL FIELD

This disclosure relates to a nano-sized low-viscosity oil-in-water type emulsion composition, a cosmetic composition comprising the same, and a method for preparing the same using an oil-in-polyol (O/P) type emulsification method.

BACKGROUND ART

Emulsion means a liquid-liquid dispersion system having a liquid phase in which at least one liquid phase immiscible with the former liquid phase is dispersed, and generally has a size distribution ranging from several micrometers to several tens micrometers.

Macroemulsion having such a particle size is in a thermodynamically unstable state, and tends to undergo separation by way of various paths such as flocculation, sedimentation, creaming, Ostwald ripening and coalescence.

When the emulsion particle size of a dispersed phase is lowered to a nano-scale, it is possible to improve the emulsion stability significantly in terms of kinetics through the Brownian movement among the particles, and to produce a low-viscosity emulsion having a high inner phase content. As a result, it is possible to provide a cosmetic agent having various feelings of use and to deliver active ingredients effectively to skin by virtue of such a small particle size.

In general, although there is a slight difference among various references, a liquid-liquid dispersion system in which particles of a dispersed phase has an average particle diameter of 20-500 nm is referred to as nanoemulsion (Flockhart, I. R. etc., Nanoemulsions derived from lanolin show promising drug delivery properties, *J. Pharm. Pharmacol.*, 50 (Supplement) 1998, 141).

Many attempts have been made to produce a nanoemulsion having fine particles and low viscosity. Particularly, a phase inversion temperature (PIT) emulsification method or a high-pressure emulsification method has been used.

More particularly, a PIT emulsification method is one using the principle of hydrophilicity reduction in a ternary composition of water, oil and a non-ionic surfactant through a decrease in hydrogen bonding between ethylene oxide as a hydrophilic group of the non-ionic surfactant and water according to an increase in temperature. Herein, the ternary composition forms an O/W type emulsion below a specific temperature and forms a W/O type emulsion above a specific temperature. Such a specific temperature is called a PIT.

In addition, a high-pressure emulsification method is one including passing particles through a high-pressure emulsifier to which high shear is applied at 1000-1500 atm to provide nanoparticles. As a high-pressure emulsifier, a microfluidizer (U.S. Pat. No. 4,533,254) capable of application of a pressure of 1000 atm or higher is frequently used.

As described above, various attempts have been made to provide fine and uniform particles. However, they are limited technically in terms of viscosity, nano-sized particle formation, maximization in visual effects of white-colored cosmetic agents or cost, and thus cosmetic producers have many difficulties in making unlimited prescriptions. In fact, the methods according to the related art cannot find use for commercial production.

Under these circumstances, many studies have been conducted to overcome the above-mentioned technical limitation and to provide a nano-sized low-viscosity emulsion.

DISCLOSURE

Technical Problem

This disclosure is directed to providing a low-viscosity white-colored oil-in-water (O/W) type nanoemulsion composition, which, otherwise, cannot be obtained according to the prior art, and a cosmetic composition comprising the same. This disclosure is also directed to solving the problems of the high-pressure emulsification method or phase inversion temperature (PIT) emulsification method used for producing an O/W type nanoemulsion composition according to the prior art, and to providing a novel method different therefrom.

Technical Solution

In one general aspect, there is provided an oil-in-water (O/W) type nanoemulsion composition, comprising: an oil phase component comprising oil and a polyethylene glycol ester-based emulsifier; and an aqueous phase component comprising a polyol or polyol derivative.

In another general aspect, there is provided a cosmetic composition including the nanoemulsion composition.

In still another general aspect, there is provided a method for preparing an O/W type nanoemulsion composition, comprising: heating an oil phase component containing oil and a polyethylene glycol ester-based emulsifier; heating a polyol or polyol derivative; introducing the oil phase component to the polyol or polyol derivative to form an oil in polyol (O/P) type gel; adding an aqueous phase component to the O/P type gel, followed by agitation; and cooling the agitated components.

Advantageous Effects

The nano-sized low-viscosity emulsion having a high inner phase content can be obtained through the method that is different from the conventional methods of phase inversion temperature emulsification or high pressure emulsification, thereby significantly improving the stability of the emulsion. In addition, the nano-emulsion composition can be applied to a variety of cosmetic compositions, and can produce cosmetic compositions having a variety of feelings of use. Further, the nano-emulsion composition has small-sized particles, and thus can deliver active ingredients to the skin effectively.

BEST MODE

According to one embodiment, the emulsion is not particularly limited as long as it has such a low viscosity that a desired degree of dispersibility can be obtained to increase the inner phase content and to deliver active ingredients effectively. For example, the emulsion may have a viscosity of 4000 cps or lower, particularly 2000 cps or lower, and more particularly 1000 cps or lower. The term 'low-viscosity' emulsion covers any emulsion from one having too low viscosity to measure it experimentally to one having the above-defined range of viscosity. When the viscosity cannot be measured experimentally, the viscosity is defined as 0. Thus, for example, the emulsion may have a viscosity of 0 to 4000 cps, particularly 1 to 2000 cps, and more particularly 5 to 1000 cps.

According to another embodiment, the emulsion is not particularly limited as long as it has a nano-scaled size and allows production of a low-viscosity emulsion while improving the emulsion stability. For example, the emulsion may have an average size of 500 nm or less, particularly 300 nm or less. For example, although the emulsion may have any average size within the above-defined range, it may have an average size of 10-500 nm, particularly 50-300 nm.

The emulsion may have a very narrow particle size distribution of 10-800 nm, particularly 100-600 nm. By virtue of this, it is possible to provide a nanoemulsion composition having a fresh feeling of use as well as excellent stability.

According to still another embodiment, the emulsion composition may be white-colored, particularly may be white-colored and creamy. When a nanoemulsion is prepared by the conventional phase inversion temperature (PIT) emulsification method as described in the following Comparative Example 2, the resultant nanoemulsion may have a translucent bluish appearance, but cannot realize a white-colored and creamy appearance. On the contrary, the emulsion composition disclosed herein may provide a visual effect through a white-colored, particularly white-colored and creamy, highly concentrated appearance.

The composition disclosed herein comprises oil and a polyethylene glycol ester-based emulsifier as an oil phase component, and polyol or a polyol derivative as an aqueous phase.

According to an embodiment, the polyethylene glycol ester-based emulsifier is not particularly limited as long as it is used generally in preparation of O/W type emulsion compositions. For example, the polyethylene glycol ester-based emulsifier may be a PEG-n glyceryl isostearate having a polymerization degree of 3-90, particularly 3-60. In addition, two or more PEG-n glyceryl isostearates having different polymerization degrees may be used in combination, for example, at a mixing ratio of 1-5:1 to 1:1-5, particularly 1-3:1 to 1:1-3.

The emulsifier may be present in an amount of 0.1-20 wt %, particularly 0.1-10 wt %, based on the total weight of the composition. When the emulsifier is used in an amount greater than 10 wt %, the oil phase has an inadequate combination ratio, resulting in excessively high viscosity. When the emulsifier is used in an amount less than 0.1 wt %, emulsifying capability is lowered and emulsion particles having an excessively large particle size are formed, resulting in degradation of the emulsion stability.

According to an embodiment, the oil is not particularly limited in type as long as it is generally used in preparation of O/W type emulsion compositions. For example, the oil may be at least one selected from the group consisting of silicone oil, ester-based oil, hydrocarbon-based oil and a mixture thereof.

For example, the oil selected from the group consisting of silicone oil, ester-based oil, hydrocarbon-based oil and a mixture thereof may be at least one selected from the group consisting of triethylhexanoin, dimethicone, cetyl octanoate, a mixture of dicaprylate with dicaprate, isopropyl miristate, tocopherol acetate and a mixture of caprylic triglyceride with capric triglyceride.

The oil may be present in an amount of 0.1-40 wt %, particularly 1-20 wt % based on the total weight of the composition. The 'oil content' means the total amount of the components forming the oil phase free from an emulsion stabilizer. When the oil is used in an amount less than 1 wt %, the resultant composition shows a decrease in moisturizing and emollient feelings, thereby reducing utility. When the oil is used in an amount greater than 20 wt %, the emulsion particles become have an increased particle size, resulting in degradation of the emulsion stability.

If desired, the composition disclosed herein may further include a pigment, fragrance, preservative or thickening agent as supplementary components for use in preparation of O/W type nanoemulsion compositions. Such supplementary components may be used in an amount of 0-20 wt % based on the total weight of the composition.

The polyol or polyol derivative is an aqueous phase component, and any polyol or derivative thereof may be used as long as it is suitable for preparation of low-viscosity nanoemulsion. For example, the polyol or polyol derivative may be at least one selected from the group consisting of glycerin, monohydric or dihydric alcohol and a mixture thereof. Particularly, the polyol or polyol derivative contained in the composition disclosed herein may be a mixture of glycerin with butylene glycol as a dihydric alcohol, but is not limited thereto.

In another aspect, there is provided a cosmetic composition including the nanoemulsion composition.

The cosmetic composition disclosed herein is not particularly limited in its formulation. For example, the cosmetic composition may be one applied to skin, mucous membranes, scalp or hair. Particularly, the cosmetic composition may be formulated into fundamental cosmetics such as skin softener, nourishing milk, lotion, cream, pack, gel, patch or spray (mist); make-up cosmetics such as lipsticks, make-up base or foundation; cleaning agents such as shampoo, rinse, body cleanser, tooth paste or mouth wash; hair treatment such as hair tonic, gel or mousse; or hair cosmetic compositions such as hair nutrient or hair dye. In addition, the cosmetic composition may be applied widely to medicines and over-the-counter medicines, such as lotion, ointment, gel, cream, patch or spray.

In still another aspect, there is provided a method for preparing an O/W type nanoemulsion composition, comprising: heating an oil phase component comprising oil and a polyethylene glycol ester-based emulsifier; heating a polyol or polyol derivative; introducing the oil phase component to the polyol or polyol derivative to form an oil in polyol (O/P) type gel; adding an aqueous phase component to the O/P type gel, followed by agitation; and cooling the agitated components.

According to the prior art, a general emulsification method in which an oil phase component and aqueous phase component are heated and agitated was used to prepare a nanoemulsion composition. However, such a method results in poor shelf stability and causes skin irritation due to an increased amount of surfactant, and thus cannot be used in practice. In addition, to solve the problem related with shelf stability, a water soluble polymer such as a carboxyvinyl polymer was used so that the emulsion stability was ensured. However, in this case, the emulsion shows an excessively high viscosity of 5000 cps or higher. Therefore, such a method does not allow formulation of emulsion.

In addition to the above method, a phase inversion temperature (PIT) emulsification method was used. However, a polyoxyethylene (POE)-based compound used generally as a non-ionic surfactant in such a PIT emulsification method provides a low PIT of approximately room temperature to 60° C., resulting in degradation of stability. In the case of cosmetics, they may undergo an increase in temperature during storage or transport, or may be stored or distributed in a hot place. Thus, an O/W type nanoemulsion may be unstabilized and undergo phase separation easily at a low PIT. Moreover, the PIT emulsification method provides nanoparticles with a translucent bluish appearance, and cannot realize a white-colored or milky white and highly concentrated appearance.

Further, a high-pressure emulsification method was used but it requires a big space, long time and expensive equipment. Thus, the method is limited in use in terms of cost. In addition, the method using a high-pressure emulsifier is applied to an emulsification system for milky liquid or cream having a high oil content. However, it is difficult to apply the method to a system having a little of or no oil, such as skim milk.

To solve the problems occurring in the related art, the method disclosed herein provides an O/W type nanoemulsion by using a polyethylene glycol ester-based emulsifier according to an oil in polyol (O/P) type emulsification method. By virtue of this, it is possible to provide an O/W type nanoemulsion to composition having low viscosity, a very small average particles size of emulsion particles, excellent stability and a highly concentrated white-colored creamy feeling.

The examples and experiments will now be described. The following examples and experiments are for illustrative purposes only and not intended to limit the scope of this disclosure.

Comparative Examples 1-3 and Example 1

Each O/W type emulsion or nanoemulsion of Comparative Examples 1-3 and Example 1 is prepared by using the compositions as shown in the following Table 1 according to each of the methods described herein (The percentage described hereinafter is % by weight).

Preparation of Comparative Example 1

1) Oil phase components and aqueous phase components are warmed separately to 75° C.
2) The oil phase components are introduced to the aqueous phase components with stirring and the resultant mixture is agitated by using a homogenizer at 3000 rpm for 5 minutes.
3) Then, the mixture is cooled and deaerated gradually.

Preparation of Comparative Example 2

1) Oil phase components are mixed and warmed to a temperature 20° C. higher than the expected phase inversion temperature to dissolve them completely.
2) Aqueous phase components are mixed and dissolved, and then warmed to the same temperature as the oil phase components.
3) The aqueous phase components (2)) are added gradually to the oil phase components (1)) while agitating them by using a homogenizer at 2000 rpm to perform emulsification, thereby providing a W/O emulsion.
4) Then, the emulsion is cooled gradually with stirring to perform phase inversion into an O/W type.
5) After determining the phase inversion, a thickener and other additives are introduced, followed by agitation.
6) After the emulsion is agitated completely, it is deaerated and cooled to 30° C. to finish the emulsion.

Preparation of Comparative Example 3

1) Oil phase components and aqueous phase components are warmed separately to 75° C.
2) The oil phase components are introduced to the aqueous phase components with stirring and the resultant mixture is agitated by using a homogenizer at 3000 rpm for 5 minutes.
3) Nanoparticles are formed from the homogenized mixture by using a microfluidizer (U.S. Pat. No. 4,533,254) at 1000 atm.
4) The nanoparticles are cooled and deaerated gradually.

Preparation of Example 1

1) Oil phase components are heated to 75° C.
2) A polyol (glycerin, butylene glycol) as one of aqueous phase components is heated to 75° C.
3) The oil phase components are introduced to the component (2)) with stirring, and the resultant mixture is agitated by using a homogenizer at 3000 rpm for 5 minutes to form an O/P type translucent gel.
4) The remaining aqueous phase components are introduced to the gel (3)) and the resultant mixture is agitated by using a homogenizer at 2500 rpm for 3 minutes,
5) followed by gradual cooling and deaeration.

TABLE 1

| | Components | Comp. Ex. 1 | Comp. Ex. 2 | Comp. Ex. 3 | Ex. 1 |
|---|---|---|---|---|---|
| Oil Phase Components | Triethylhexanoin | 2 | 2 | 2 | 2 |
| | Cetyl ethylhexanoate | 2 | 2 | 2 | 2 |
| | Dimethicone | 3 | 3 | 3 | 3 |
| | Cetearyl alcohol | 0.3 | 0.3 | 0.3 | 0.3 |
| | Polyglyceryl-3 methyl glucose distearate | 1.5 | 0 | 0 | 0 |
| | PEG-100 stearate | 0.5 | 0 | 0 | 0 |
| | Ceteareth-12 | 0 | 1.5 | 0 | 0 |
| | Ceteareth-20 | 0 | 0.5 | 0 | 0 |
| | PEG-5 rapeseed sterol | 0 | 0 | 1.5 | 0 |
| | Hydrogenated lecithin | 0 | 0 | 0.5 | 0 |
| | PEG-20 glyceryl isostearate | 0 | 0 | 0 | 1.5 |
| | PEG-40 glyceryl isostearate | 0 | 0 | 0 | 0.5 |
| Aqueous phase components | Purified water | balance | balance | balance | balance |
| | Glycerin | 2 | 2 | 2 | 2 |
| | Butylene glycol | 4 | 4 | 4 | 4 |

Test Example 1

Each O/W type emulsion or nanoemulsion according to Comparative Examples 1-3 and Example 1 is determined for particle size, appearance and viscosity during preparation, and the results are shown in the following Table 2.

TABLE 2

| | Comp. Ex. 1 | Comp. Ex. 2 | Comp. Ex. 3 | Ex. 1 |
|---|---|---|---|---|
| Particle size (average) | 12 μm | 250 nm | 280 nm | 275 nm |
| Viscosity (cps) | 8700 | 120 | 80 | 150 |
| Appearance | milky white | bluish | turbid | white |

Referring to the results of Table 2, it can be seen that Comparative Examples 2 and 3 (except Comparative Example 1) and Example 1 provide a low-viscosity nanoemulsion having a desired viscosity of 1000 cps or less and a particle size of 500 nm or less. In terms of appearance, Comparative Example 1 and Example 1 provide a desired white-colored emulsion.

Test Example 2

Determination of Emulsion Stability

Each O/W type cosmetic agent according to Comparative Examples 1-3 and Example 1 is used as a test sample, and determined for emulsion stability by observing whether creaming or oil separation occurs or not while each emulsion is stored at room temperature, at 45° C. and in a circulating thermostat bath for 5 days, 10 days, 15 days and one month. The results are shown in the following Table 3.

TABLE 3

|  |  | Comp. Ex. 1 | Comp. Ex. 2 | Comp. Ex. 3 | Ex. 1 |
|---|---|---|---|---|---|
| Room Temperature (RT) | 5 days | good | good | good | good |
|  | 10 days | good | good | good | good |
|  | 15 days | good | creaming | creaming | good |
|  | 1 month | good | creaming | creaming | good |
| 45° C. | 5 days | good | good | good | good |
|  | 10 days | good | creaming | good | good |
|  | 15 days | good | creaming | creaming | good |
|  | 1 month | creaming | oil separation | oil separation | good |
| Circulating theremostat | 5 days | good | good | good | good |
|  | 10 days | good | good | good | good |
|  | 15 days | good | creaming | creaming | good |
|  | 1 month | good | creaming | creaming | good |

As can be seen from Table 3, the O/W nanoemulsion according to Example 1 ensures higher stability at room temperature, at a high temperature and in a circulating condition, as compared to the O/W type emulsions according to Comparative Examples 1-3. In other words, it is possible to obtain a stable nano-sized low-viscosity O/W type white-colored emulsion by using an oil in polyol (O/P) emulsification method in the preparation an O/W type nanoemulsion.

While the exemplary embodiments have been shown and described, it will be understood by those skilled in the art that various changes in form and details may be made thereto without departing from the spirit and scope of this disclosure as defined by the appended claims.

The invention claimed is:

1. A method for preparing an oil-in-water (O/W) type nanoemulsion composition, comprising:
   heating an oil phase component to 75° C., wherein the oil phase component consists essentially of a mixture of triethylhexanoin, cetyl ethylhexanoate, dimethicone, cetearyl alcohol, PEG-20 glyceryl isostearate and PEG-40 glyceryl isostearate;
   heating a polyol or polyol derivative to 75° C., wherein the polyol or polyol derivative consists essentially of a mixture of glycerin and butylene glycol;
   introducing the oil phase component to the polyol or polyol derivative to form an oil-in-polyol (O/P) type gel;
   adding an aqueous phase component to the O/P type gel, followed by agitation; and
   cooling the agitated components,
   wherein the nanoemulsion has an average particle size of 10-500 nm.

2. The method for preparing an oil-in-water (O/W) type nanoemulsion composition according to claim 1, wherein the nanoemulsion has a viscosity of 0-4000 cps.

3. The method for preparing an oil-in-water (O/W) type nanoemulsion composition according to claim 1, wherein the nanoemulsion is white-colored.

4. The method for preparing an oil-in-water (O/W) type nanoemulsion composition according to claim 1, wherein the PEG-20 glyceryl isostearate and PEG-40 glyceryl isostearate are present in an amount of 0.1-10 wt % based on the total weight of the composition.

5. The method for preparing an oil-in-water (O/W) type nanoemulsion composition according to claim 1, wherein the triethylhexanoin and dimethicone are present in an amount of 1-20 wt % based on the total weight of the composition.

6. The method for preparing an oil-in-water (O/W) type nanoemulsion composition according to claim 1, wherein the composition is a cosmetic composition.

* * * * *

UNITED STATES PATENT AND TRADEMARK OFFICE
CERTIFICATE OF CORRECTION

| | |
|---|---|
| PATENT NO. | : 9,132,091 B2 |
| APPLICATION NO. | : 13/635784 |
| DATED | : September 15, 2015 |
| INVENTOR(S) | : Sung Il Park et al. |

Page 1 of 1

It is certified that error appears in the above-identified patent and that said Letters Patent is hereby corrected as shown below:

In the Specification
· At column 4, line 1, delete "become".
· At column 7, line 19, delete "theremostat", insert --thermostat--.
· At column 7, line 31, after the word preparation, insert --of--.

Signed and Sealed this
Twenty-second Day of March, 2016

Michelle K. Lee
*Director of the United States Patent and Trademark Office*